(12) United States Patent
Martinez

(10) Patent No.: US 10,973,577 B1
(45) Date of Patent: Apr. 13, 2021

(54) LASER HAIR TREATMENT SYSTEM

(71) Applicant: Stephan Martinez, Haltom City, TX (US)

(72) Inventor: Stephan Martinez, Haltom City, TX (US)

( * ) Notice: Subject to any disclaimer, the term of this patent is extended or adjusted under 35 U.S.C. 154(b) by 949 days.

(21) Appl. No.: 15/466,536

(22) Filed: Mar. 22, 2017

Related U.S. Application Data

(63) Continuation-in-part of application No. 14/225,097, filed on Mar. 25, 2014, now abandoned.

(60) Provisional application No. 61/805,138, filed on Mar. 25, 2013.

(51) Int. Cl.
    *A61B 18/20* (2006.01)
    *A61B 18/00* (2006.01)

(52) U.S. Cl.
    CPC .. *A61B 18/203* (2013.01); *A61B 2018/00321* (2013.01); *A61B 2018/00476* (2013.01); *A61B 2018/00642* (2013.01); *A61B 2018/2015* (2013.01)

(58) Field of Classification Search
    CPC ............ A61H 2205/021; A61N 5/0617; A61B 2018/00321; A61B 2018/00476; A61B 18/203
    See application file for complete search history.

(56) References Cited

U.S. PATENT DOCUMENTS

| | | | |
|---|---|---|---|
| 1,821,979 A | 9/1931 | Lowen | |
| 2,099,744 A * | 11/1937 | Lohr | A61H 9/005 601/17 |
| 5,228,431 A | 7/1993 | Giaretto | |
| 6,666,878 B2 * | 12/2003 | Carlgren | A61N 5/0617 607/88 |
| 7,559,944 B2 | 7/2009 | Whang | |
| 7,722,656 B1 | 5/2010 | Segal | |
| 7,959,656 B2 | 6/2011 | Myeong | |
| 8,192,473 B2 | 6/2012 | Tucker | |
| 2008/0114418 A1 | 5/2008 | Myeong | |
| 2010/0298745 A1 * | 11/2010 | Liu | A61H 9/0057 601/12 |
| 2013/0184693 A1 | 7/2013 | Neev | |
| 2014/0073996 A1 * | 3/2014 | Jaguan | A61N 5/0618 601/15 |

(Continued)

OTHER PUBLICATIONS

Non-Final Office Action from U.S. Patent and Trademark Office dated Jul. 26, 2016 from corresponding U.S. Appl. No. 14/225,097.

(Continued)

*Primary Examiner* — LaToya M Louis

(74) *Attorney, Agent, or Firm* — Law Office of Jeff Williams PLLC; J. Oliver Williams

(57) ABSTRACT

A system and method for hair treatment. The system includes a vacuum system configured to apply negative pressure of the scalp of a user and a laser system operably associated with the vacuum system and configured to emit light to a hair follicle of the user to promote hair growth. The method includes promoting blood flow on the scalp with the vacuum system and stimulating hair growth with the laser system. The system and method being routed through a dual layered helmet configured to include a central vacuum chamber for the equal distribution of pressure to the scalp.

19 Claims, 8 Drawing Sheets

(56) References Cited

U.S. PATENT DOCUMENTS

2016/0310757 A1* 10/2016 Pepitone .............. A61N 5/0616

OTHER PUBLICATIONS

Final Office Action from U.S. Patent and Trademark Office dated Nov. 18, 2016 from corresponding U.S. Appl. No. 14/225,097.
Non-Final Office Action from U.S. Patent and Trademark Office dated Sep. 8, 2016 from corresponding U.S. Appl. No. 14/566,713.

* cited by examiner

LASER HAIR TREATMENT SYSTEM

CLAIM OF PRIORITY

This application is a continuation-in-part of and claims the benefit of U.S. application Ser. No. 14/225,097, filed 25 Mar. 2014, which claims the benefit of U.S. Provisional Application No. 61/805,138, filed 25 Mar. 2013. The information contained therein is hereby incorporated by reference.

BACKGROUND

1. Field of the Invention

The present invention generally relates to hair-loss treatments and more specifically to hair-loss treatments involving lasers.

2. Description of Related Art

Laser hair-loss treatment is well known in the art. For example, U.S. Pat. No. 6,497,719 to Pearl et al. discloses and claims a hand-held laser device that stimulates hair growth. The Pearl et al. device provides distributed laser light to the scalp while simultaneously parting the user's hair to ensure that the laser light contacts the user's scalp. A unique beam splitting reflector splits a single laser beam to ensure that energy from the laser beam is evenly distributed.

In addition to that U.S. Pat. No. 6,666,878 to Carlgren discloses and claims a method of stimulating the hair follicles of a skin area by radiation of light.

Also U.S. Pat. No. 7,194,316 to Bousfield et al. discloses and claims a handheld head treatment device and method for reducing hair loss and stimulating hair growth by supplying current and laser light to a user's head. The Bousfield et al. device includes a current generator disposed within a housing configured to output a current for passage into the user's head and a laser source and guide means disposed within the housing configured to output and direct respective portions of the laser beam outward from the hair treatment device toward the user's head when the hair treatment device is in use.

Finally U.S. Pat. No. 7,201,764 also to Pearl et al. discloses and claims a hand-held laser device that stimulates hair growth. This second device disclosed by Pearl et al., provides distributed laser light to the scalp while simultaneously parting the individual's hair to ensure that the laser light contacts the individual's scalp. A unique beam splitting reflector splits a single laser beam to ensure that energy from the laser beam is evenly distributed. The reflector is mechanically aligned with the laser source and has a zigzag structure which mechanically deflects portions of the beam as it passes over the peaks of the reflector.

Despite all the efforts listed above prior art patents describe structures that are either not truly effective or convenient or else involve complicated, expensive, and overly difficult assembly and/or disassembly parts and procedures. Other devices have been advertised on various media but never patented or described into a printed publication.

Although great strides have been made in the area of hair-loss treatments, many shortcomings remain.

DESCRIPTION OF THE DRAWINGS

The novel features believed characteristic of the embodiments of the present application are set forth in the appended claims. However, the embodiments themselves, as well as a preferred mode of use, and further objectives and advantages thereof, will best be understood by reference to the following detailed description when read in conjunction with the accompanying drawings, wherein:

Figure 1:
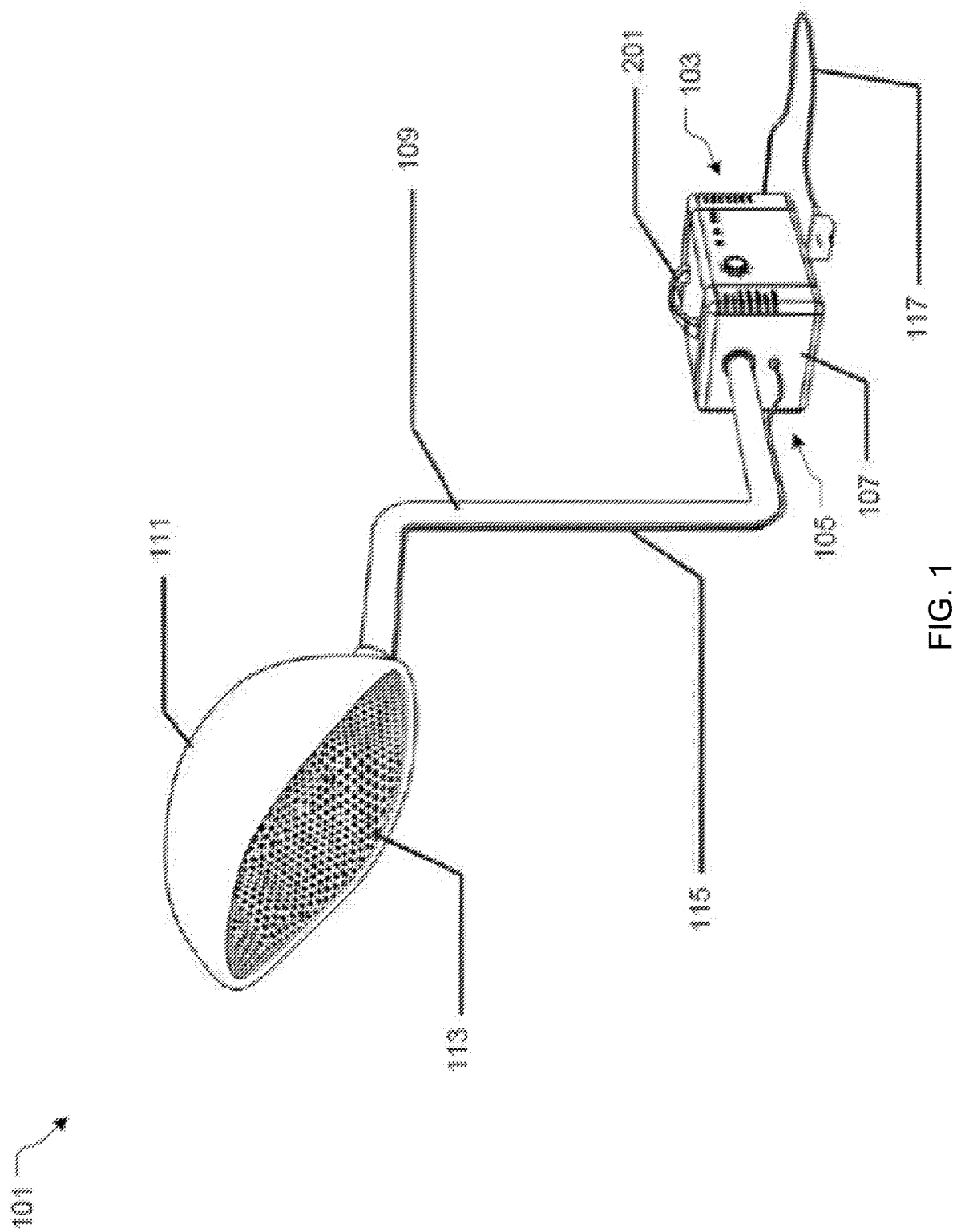
FIG. 1 is an oblique view of the system in accordance with the preferred embodiment of the present application.

While the system and method of use of the present application is susceptible to various modifications and alternative forms, specific embodiments thereof have been shown by way of example in the drawings and are herein described in detail. It should be understood, however, that the description herein of specific embodiments is not intended to limit the invention to the particular embodiment disclosed, but on the contrary, the intention is to cover all modifications, equivalents, and alternatives falling within the spirit and scope of the present application as defined by the appended claims.

DETAILED DESCRIPTION OF THE PREFERRED EMBODIMENT

Illustrative embodiments of the system and method of use of the present application are provided below. It will of course be appreciated that in the development of any actual embodiment, numerous implementation-specific decisions will be made to achieve the developer's specific goals, such as compliance with system-related and business-related constraints, which will vary from one implementation to another. Moreover, it will be appreciated that such a development effort might be complex and time-consuming, but would nevertheless be a routine undertaking for those of ordinary skill in the art having the benefit of this disclosure.

The system and method of use in accordance with the present application overcomes one or more of the above-discussed problems commonly associated with conventional hair treatment systems. Specifically, the present invention is a lightweight, rigid helmet configured to provide directed laser treatment and applied vacuum pressure across the scalp. The rigid helmet is connected to a separate device to generate the power for the laser treatment and the vacuum for the alternating vacuum pressures within the helmet. As seen more clearly through FIGS. 4-8, the helmet contains diffused laser diodes around the interior which shine directly onto the scalp, energizing the cells of the scalp and hair roots to promote hair growth. The vacuum machine applies a negative vacuum to the entire scalp to increase blood flow to the scalp to assist in hair growth. It is then the principal object of the present system and method to promote hair growth. It is a secondary objective of the present system and method to restore health to the hair. It is an additional objective of the present system and method to prevent hair loss. It is a final objective of the present system and method to facilitate hair re-growth without harmful steroids or other ingested medicines. These and other unique features of the system and method of use are discussed below and illustrated in the accompanying drawings.

The system and method of use will be understood, both as to its structure and operation, from the accompanying drawings, taken in conjunction with the accompanying description. Several embodiments of the system are presented herein. It should be understood that various components, parts, and features of the different embodiments may be combined together and/or interchanged with one another, all of which are within the scope of the present application, even though not all variations and particular embodiments are shown in the drawings. It should also be understood that the mixing and matching of features, elements, and/or functions between various embodiments is expressly contemplated herein so that one of ordinary skill in the art would appreciate from this disclosure that the features, elements, and/or functions of one embodiment may be incorporated into another embodiment as appropriate, unless described otherwise.

Figure 2:
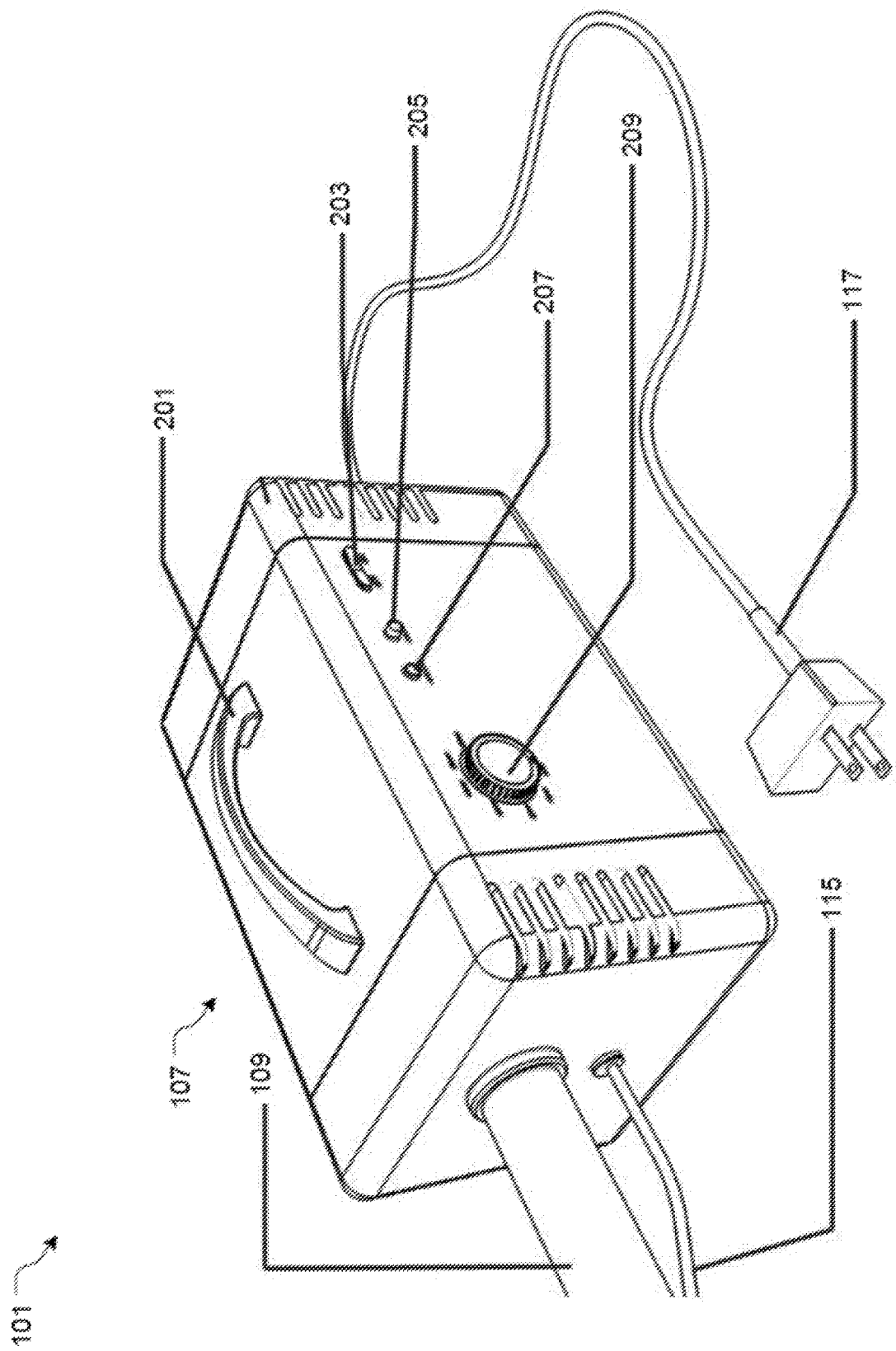
FIG. 2 is an oblique view of the portable container of the system of FIG. 1.
Figure 3:
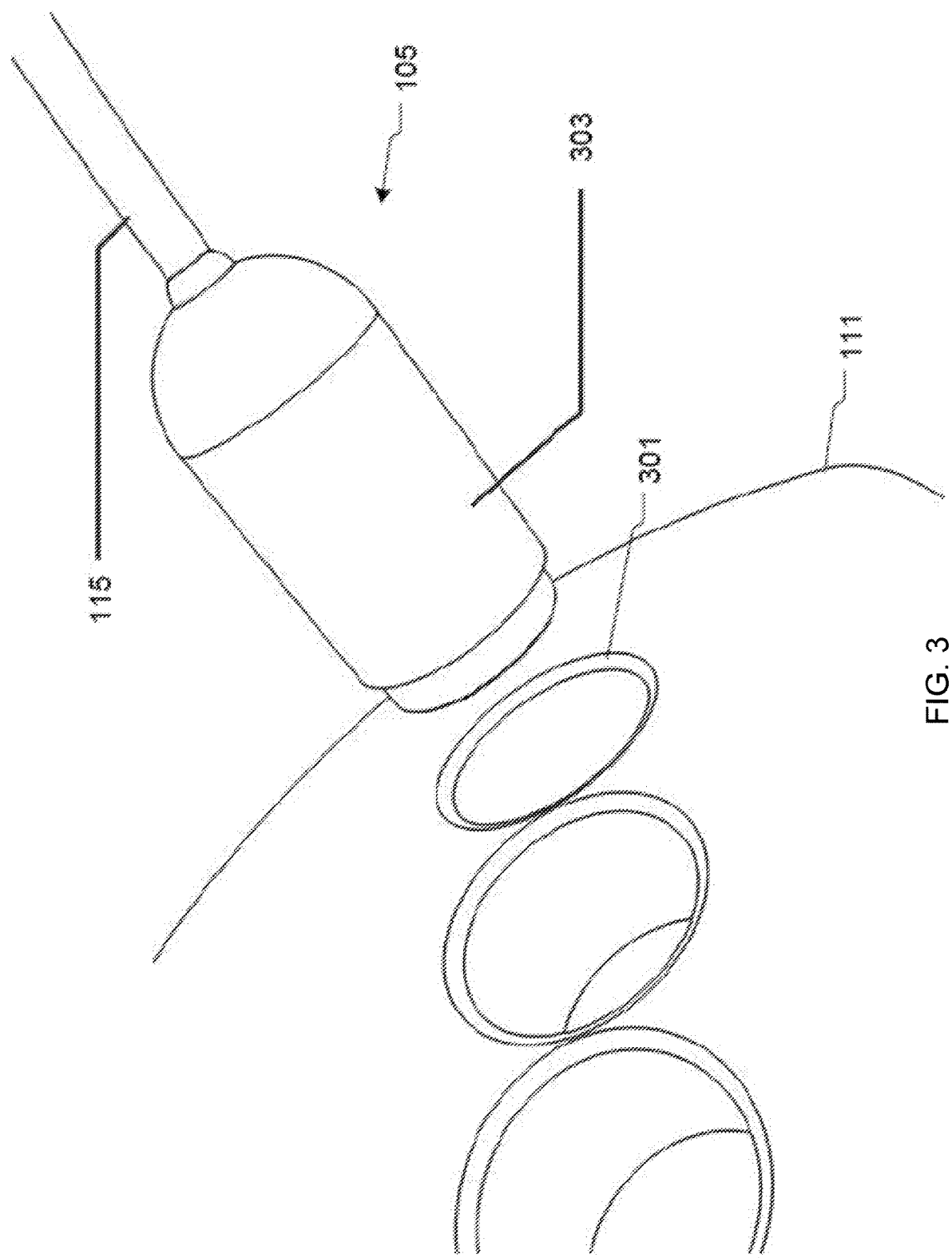
FIG. 3 is an oblique partial view of a helmet and laser system of the system of FIG. 1.

Referring now to the drawings wherein like reference characters identify corresponding or similar elements throughout the several views, FIGS. 1-3 depict various oblique views of a laser hair treatment system 101 in accordance with a preferred embodiment of the present application. It will be appreciated that system 101 overcomes at least one of the above-listed problems commonly associated with the conventional hair treatment systems.

It will be appreciated that the hair treatment system 101 of the present application is a lightweight portable system that utilizes both vacuum pressure and a laser to induce hair growth. The vacuum increases the blood circulation around the scalp, while the laser increases both blood flow and excites hair growth. The vacuum pressure also dilates the skin which permits the laser to penetrate deeper and easier into the skin.

To achieve this feature, system 101 includes a helmet 111 and one or more of a vacuum system 103 and a laser system 105 carried within a portable container 107. System 101 addresses the problem of hair loss caused by a decreased blood flow to the scalp and a buildup of DHT in the scalp. The system 101 addresses these problems in two ways: low level laser therapy is administered to the scalp which energizes the root of the hair follicles and increases blood flow to the scalp while blood flow is further stimulated through alternating negative and ambient pressure on the scalp. The treatment received by system 101 is generally administered for several minutes daily for several weeks, which results in the restoration of hair growth, in the prevention of hair loss and in the reduction of headaches and other stress related conditions. Further detail description of these features are provided below.

Vacuum system 103 includes a vacuum hose 109 in communication with helmet 111. Vacuum system 103 is configured to induce a negative ambient pressure adjacent the scalp of a user. Vacuum hose 109 extends between container 107 and helmet 111. Vacuum hose 109 carries the negative pressure to helmet 111. Vacuum pressure contacts the scalp through one or more ports (see FIG. 3) along an interior surface of helmet 111. During use, the user will place helmet 111 on the head and vacuum system 103 will apply negative pressure against the scalp through the ports (i.e. a plurality of holes) in communication with the hose 109 and helmet 111. In the exemplary embodiment, an optional cushion 113 is provided for comfort. Cushion 113 is more clearly described and illustrated in later figures.

Also in communication with helmet 111 is the laser system 105, which channels laser energy from container 107 to helmet 111 via a laser cord 115. In the preferred embodiment, cord 115 and hose 109 are attached at selective locations so as to permit them to travel together and bend together. This assists in maintaining uniformity and order with the plurality of hoses/cords that run between helmet 111 and container 107. A power cord 117 is operably attached to container 107 and is utilized to permit the transfer of power to both the vacuum system 103 and laser system 105 carried therein container 107. Power cord 117 is configured as a plug for acceptance into a socket to receive power (i.e. A/C power) from a power grid. Such power can be provided directly via a plug in the wall or through a separate device plugged into a wall.

In particular with FIG. 2 in the drawings, container 107 is depicted having a handle 201 for transportation, a laser power switch 203, a laser indicator 205, a vacuum indicator 207, and a vacuum strength knob 209. It will be appreciated that the systems carried within container 107 are thus manipulated via one or more knobs and/or switches to achieve the desired results. Switch 203 and knob 209 permit a user to select a desired power level and vacuum pressure best suited for the present user. Indicators 205 and 207 are configured to provide feedback to a user or operator as to the level or strength of the power and vacuum being applied to the scalp.

In particular with FIG. 3 in the drawings, the association of helmet 111 and laser system 105 is illustrated. Helmet 111 includes one or more ports 301 configured to receive and fasten a laser diode 303. The diffused laser diodes 303 are configured to shine laser light around the interior of helmet, which in turn energizes the cells of the scalp and the hair roots to promote hair growth. It is preferred that each diode is directed perpendicular to the scalp, such that the laser diode 303 at any location within helmet 111 is directed to the scalp. The diodes around the internal layer point toward the center of a theoretical sphere.

It is of note that not all the ports 301 need to contain diode 303. Diodes 303 are selectively spaced throughout helmet 111 but preferably do not necessarily fill all ports 301. Open ports 301 are used to provide the negative pressure to the scalp from vacuum system 103. It is understood that some embodiments may permit that diode 303 partially fills port 301 thereby also allowing for vacuum pressure to be applied through a port using diode 303.

Referring now also to FIGS. 4-8 in the drawings, an alternative embodiment of helmet 111 is illustrated. Helmet 401 is another exemplary embodiment of helmet 111 and includes the same function and features as previously described. As noted previously, system 401 is configured as a single unit wherein vacuum system 103 and laser system 105 are integrally coupled to helmet 111/401. Vacuum system 103 is configured to apply a negative pressure to the scalp of a user to promote blood flow to the scalp. Laser system 105 is operably associated with vacuum system 103 and configured to emit a controlled light to the scalp of the user which in turn promotes hair growth. Helmet 401 is configured to surround and contact a portion of the scalp, vacuum system 103 and laser system 105 are integrally coupled to a portion of helmet 401. Selective operation of the vacuum system and laser system to the scalp is configured to promote the health and growth of hair.

Helmet 401 is composed of an internal shell 403 and an external shell 405. Helmet 401 is configured to communicate with laser system 105 and vacuum system 103. Vacuum pressure is introduced between shells 403 and 405 and allowed to distribute vacuum over the entire scalp when worn by the user.

Figure 4:
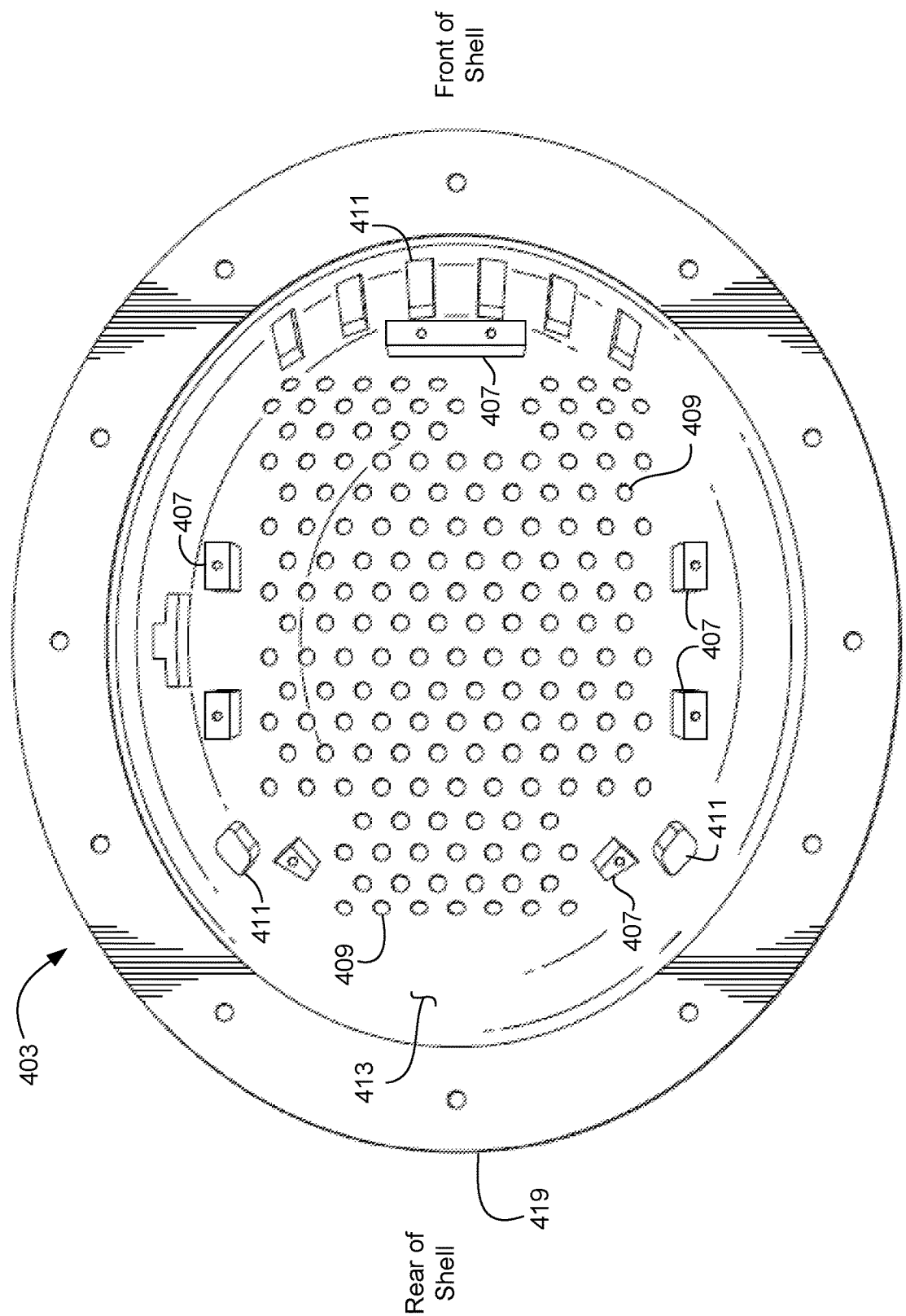
FIG. 4-8 are assorted views of an alternative embodiment to the helmet of FIG. 3.

Referring now in particular to FIG. 4, an internal view of shell 403 is shown. Shells 403 and 405 are concaved so as to form to the relative shape of a scalp. Helmet 401 is configured to rest on a user's head and selectively apply an alternating vacuum pressure and low level laser therapy through a plurality of diodes similar to diode 303. To accomplish this, shell 403 includes a plurality of mounts 407 for supporting one or more pads (see FIG. 7). Shell 403 also includes ports 409 (similar to ports 301) and apertures 411. Ports 409 are configured to receive and house the diodes from the laser system and apertures 411 are configured to permit a uniform application of vacuum pressure around the scalp.

Ports 409 are perpendicularly aligned with the inner surface 413 of shell 403 so as to permit the diodes to shine the laser light uniformly onto the scalp. Ports 409 are aligned in an alternating pattern such that the laser lights from the diodes do not touch each other. Apertures 411 are located around the periphery of shell 403 and allow for the equal application of a pressure differential on the scalp. As seen in FIG. 4, apertures 411 are slots located at the front of shell 403 and apertures 411 are also located in the rear of shell 403.

Figure 5:
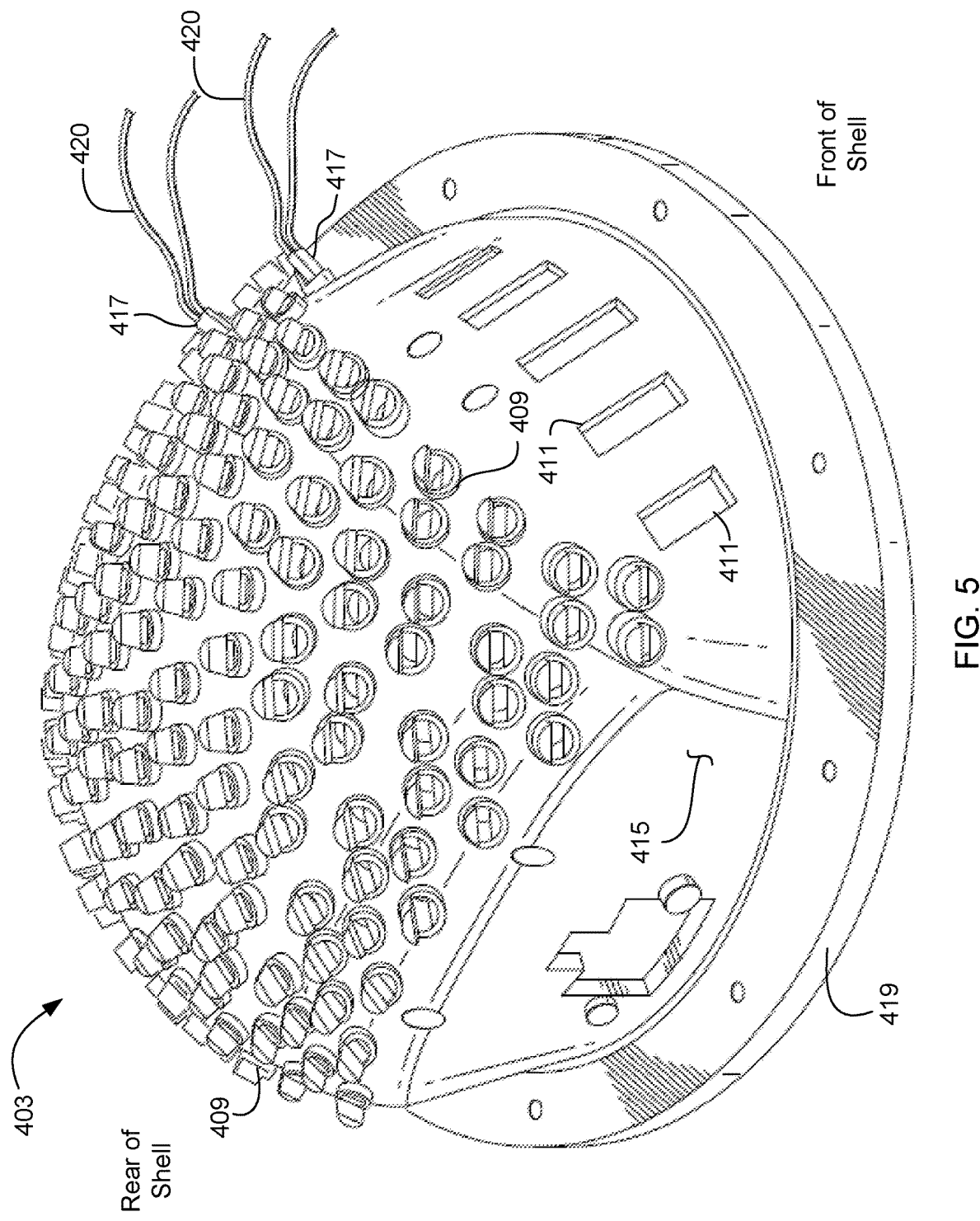
Figure 6:
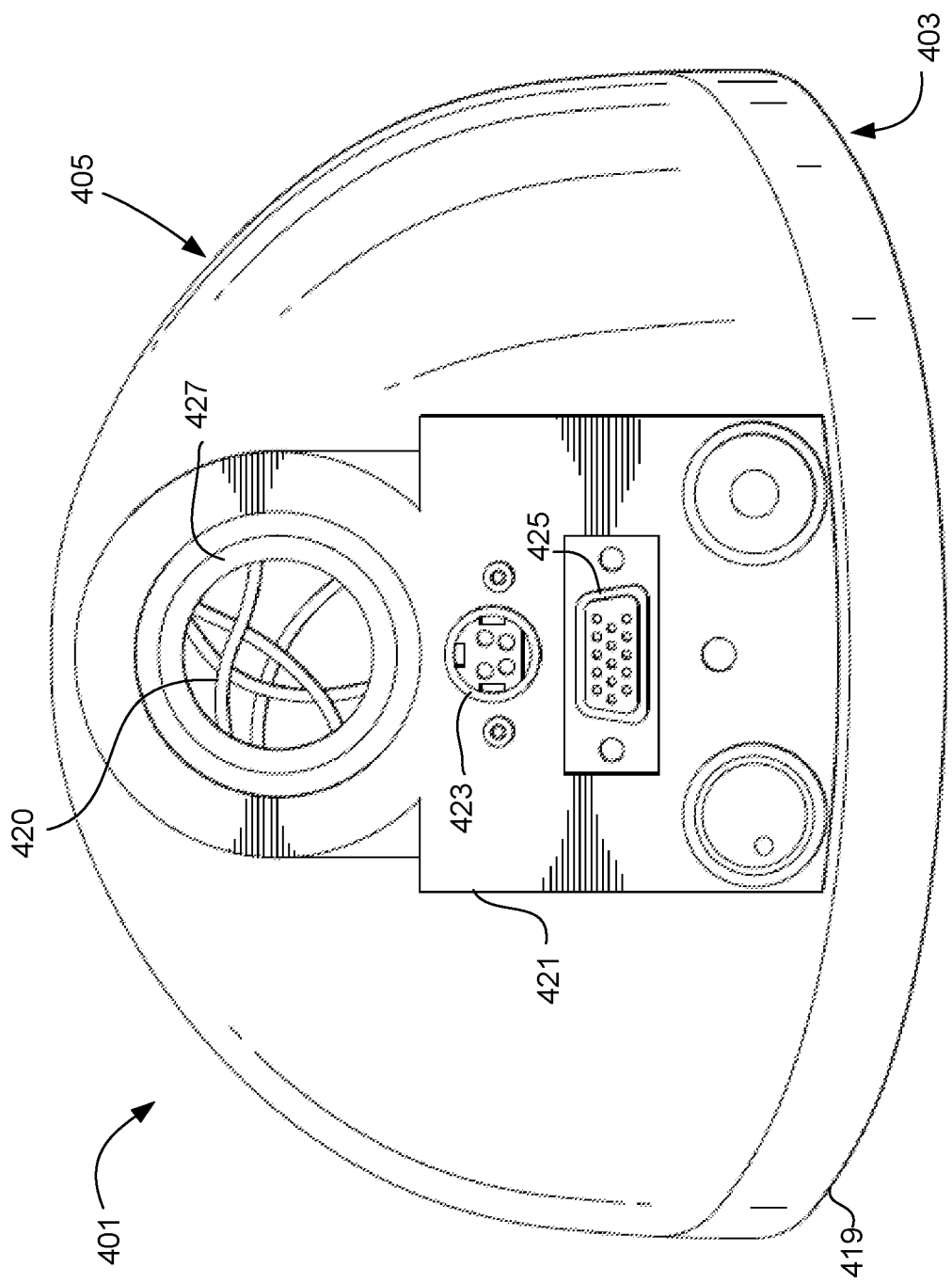

Referring now to FIG. 5, wherein an outer view of shell 403 is illustrated. Ports 409 are configured to extend out from surface 415 of shell 403 so as to provide a housing and support for each diode. Diodes 417 are illustrated in an engaged position into the housing of port 409. The wires 420 are run along surface 415 toward the rear of shell 403. In application, the wires 420 of each diode are carefully combined and routed between the housings of neighboring port housings.

A bottom flange 419 is used to secure shell 403 to that of shell 405. As seen now in particular with FIG. 6, the rear of helmet 411 is shown wherein shell 403 is coupled to shell 405. Shell 405 is placed over the external surface 415 of shell 403. Shell 405 is configured to conceal the internal wires 420 and diodes 417 of helmet 401. It is understood that laser power cord 115 couples to a portion of the external shell of helmet 111 and is then dispersed into one or more individual wires 420 which are used to electrically and operably engage each diode 417. At the rear of helmet 401 is a communication panel 421 configured to house selected connectors and serve as a connection location for the vacuum system 103 and the laser system 105. Connector 423 is configured to releasably couple to laser cord 115. The wires 420 from each diode 417 are communicated to connector 423. By connecting laser cord 115 to connector 423, power is provided to each diode 417.

Connector 425 is located in communication panel 421 and is configured to provide output data regarding the performance of helmet 401. Communication panel 421, vacuum system 103, and/or laser system 105 are configured to include sensing capabilities so as to monitor the real-time output of pressure and energy levels through helmet 401 and compare such information to that of a requested/desired level through the one or more operative controls of laser system 105 and vacuum system 103. Output data is collected through connector 425 for analysis.

Vacuum connector 427 is located on communication panel 421 and is configured to releasably couple to hose 109 so as to maintain a desired pressure. Connector 427 is configured to permit the evacuation of, and introduction of, air as necessary in order to regulate the vacuum pressure between shell 403 and shell 405.

Figure 7:
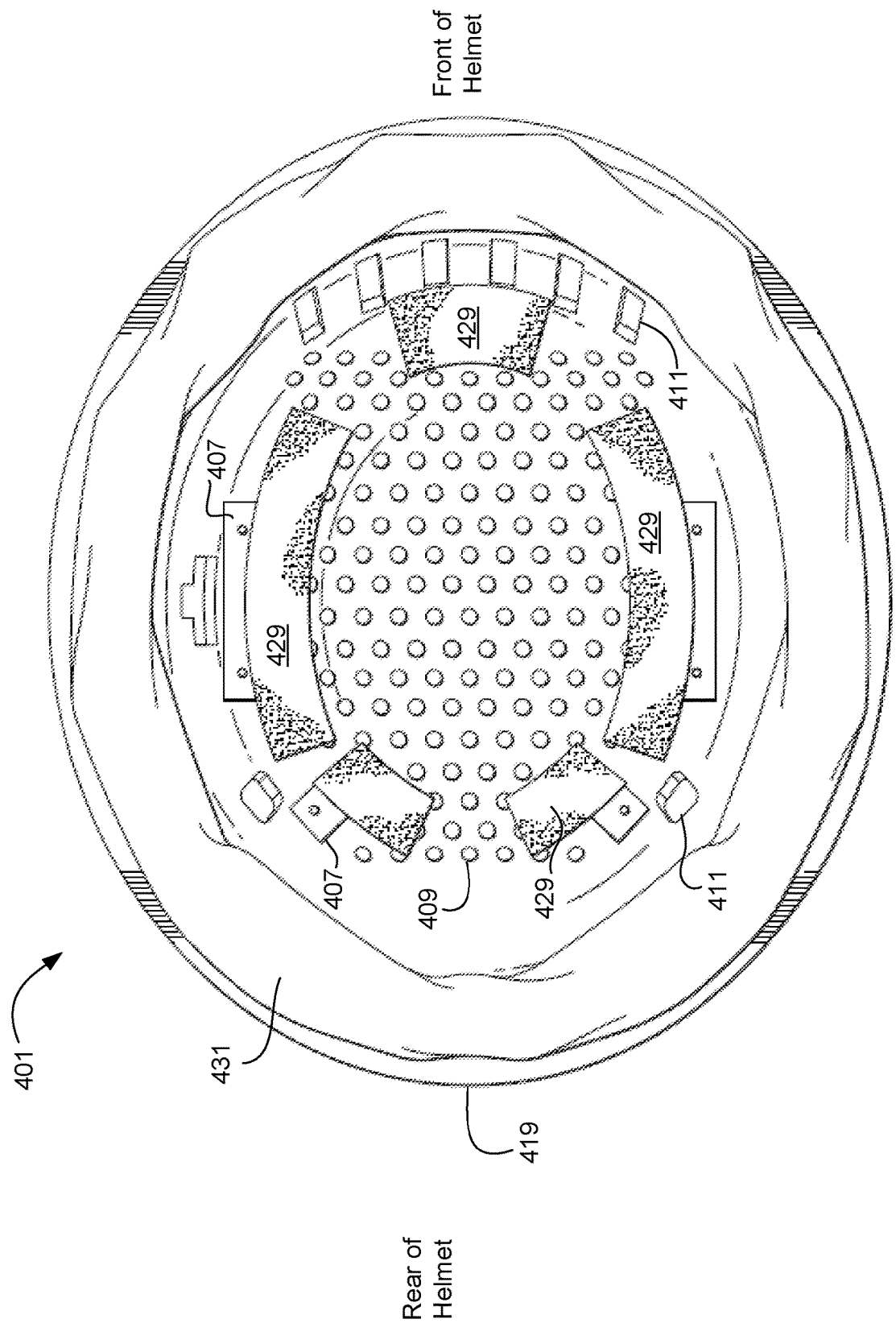

Referring now to FIG. 7 in the drawings, an internal view of helmet 401 is illustrated. Some of the different features seen in this figure compared to that of FIG. 4 is the inclusion of pads 429 and skirting 431. Pads 429 are configured to releasably couple to mounts 407 and are designed to elevate helmet 401 a selected distance away from a user's scalp. The pads 429 are designed for comfort of the user. It is understood that pads 429 may be aligned in different locations on mounts 407 to adjust their location in relation to each port 409. Depending on the location of the scalp where stimulation is needed, pads 429 may be adjusted to move inward or outward toward the periphery of shell 403.

Skirting 431 is coupled to shell 403 adjacent flange 419. Skirting 431 is coupled around a base edge portion of helmet 401 and is configured to provide comfort to the scalp of the user and act as a seal in order to generate a controlled vacuum pressure against the scalp. Skirting 431 prevents the escape of vacuum pressure and laser light from underneath helmet 401. Skirting 431 is a flexible member that is designed to create a seal around the scalp. Materials may be used that conventionally prevent the passage of air, such as rubber for example. Other materials may be used. Skirting 431 may also be configured to stretch around its edges to allow it to accommodate various head sizes while maintaining a proper seal.

Figure 8:
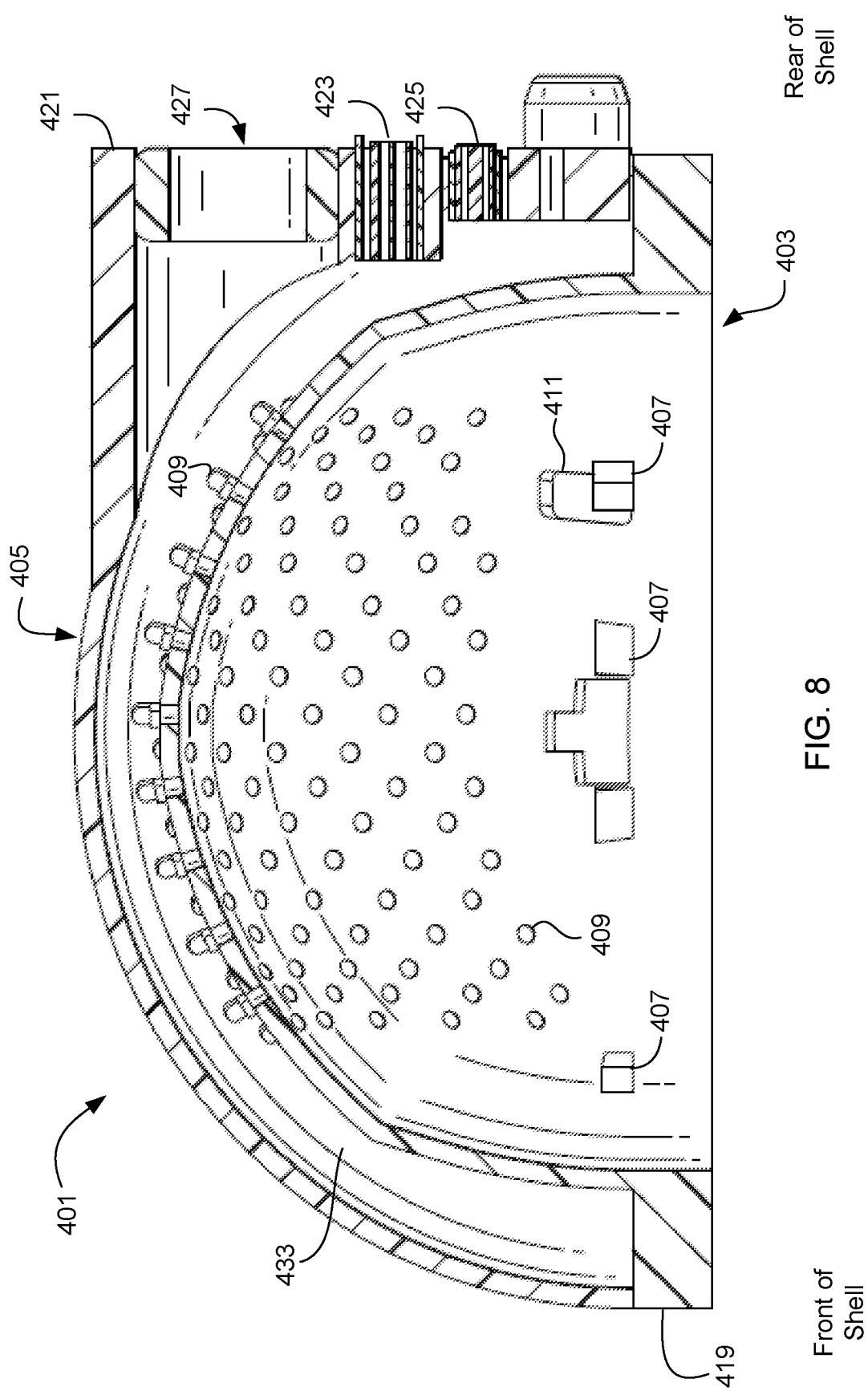

Referring now also to FIG. 8 in the drawings, a section view of helmet 401 is provided. Wires 420, diodes 417, skirting 431, and pads 407 are not shown for clarity purposes. As noted previously, helmet 401 is configured to include shells 403 and 405. When combined, shells 403 and 405 create a vacuum chamber 433 there between that is in fluid communication with vacuum connector 427. Vacuum chamber 433 is configured to extend around the full circumference of shell 403 and shell 405.

Vacuum system 103 is configured to introduce a vacuum pressure through hose 109 and into vacuum chamber 433 (void space). Vacuum ports 411 are located around the circumference of shell 403 to selectively and evenly distribute this pressure over the scalp. In so doing, pressure gradients are administered both within shell 403 and within chamber 433 simultaneously. Of note is that the vacuum pressure is equally applied to both ends of diodes 417. Ports 409 are located along surface 413 but extend into chamber 433. Diodes 417 are secured in ports 409 and may or may not be sealed. Sealing of diodes 417 are not necessary. Additionally, not all ports 409 may be filled with a diode 417. Use and configuration of diodes 417 may be selectively tailored to suit the needs of the user. Therefore it is understood that when not in use, or when not sealed in ports 409, vacuum pressure may in fact pass through ports 409 between chamber 433 and the area between the scalp and surface 413. Allowing vacuum pressure to pass through ports 409 further aids to assist in maintaining a uniform and equal pressure gradient across the scalp.

It will be appreciated that the laser hair growth treatment is a FDA-approved treatment for hair loss. It has been found that three minute sessions every one or two weeks produced significant hair growth, compared to non-treated lesions in 47% of patients. This therapy is known to increase metabolism at the cellular level, causing accelerated ATP production; protein synthesis; DNA and RNA formation; and other positive markers. At the tissue level, circulation increases during and after the administration of low level laser therapy; new blood and lymphatic vessels are formed; and collagen synthesis is enhanced.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent The particular embodiments disclosed above are illustrative only, as the embodiments may be modified and practiced in different but equivalent manners apparent to those skilled in the art having the benefit of the teachings herein.

It is therefore evident that the particular embodiments disclosed above may be altered or modified, and all such variations are considered within the scope and spirit of the application. Accordingly, the protection sought herein is as set forth in the description. Although the present embodiments are shown above, they are not limited to just these embodiments, but are amenable to various changes and modifications without departing from the spirit thereof.

What is claimed is:

1. A system for hair treatment, comprising:
a vacuum system configured to selectively apply negative pressure to a scalp of a user;
a laser system operably associated with the vacuum system and configured to emit a light through one or more diodes toward the scalp of the user to promote hair growth; and
a helmet in communication with the vacuum system and the laser system, the helmet having:
an internal shell with one or more ports to locate the one or more diodes of the laser system, the internal shell also including one or more vacuum apertures, the one or more ports and the one or more vacuum apertures extending there through the internal shell; and
an external shell surrounding a periphery of the internal shell so as to define a central vacuum chamber between the internal shell and the external shell, the vacuum chamber is configured to house the negative pressure applied by the vacuum system and distribute it through the internal shell to the scalp.

2. The system of claim 1, wherein the negative pressure is configured to surround the internal shell.

3. The system of claim 1, wherein the negative pressure is exerted on opposite ends of the one or more diodes, the diodes extending through the internal shell.

4. The system of claim 1, wherein the negative pressure passes through the one or more vacuum apertures and at least one of the one or more ports.

5. The system of claim 1, wherein the helmet is configured to transmit output data through a first connector in communication with the external shell.

6. The system of claim 5, wherein the helmet is configured to monitor real-time output of pressure and energy through the laser system and the vacuum system.

7. The system of claim 6, wherein the helmet is configured to compare the real-time output data to requested data levels.

8. The system of claim 1, wherein the light is configured to be administered as the vacuum system alternates negative and ambient pressures on the scalp.

9. A method to promote hair growth on a scalp of a user, comprising the steps of:
activating a vacuum system configured to generate pressure variations;
locating a helmet on the user, the helmet having an internal shell and an external shell, the helmet in communication with the vacuum system, the pressure variations being exhibited through a central vacuum chamber between the shells and through one or more vacuum apertures around the internal shell;
promoting blood flow on the scalp by alternating ambient and negative pressures on the scalp through the one or more vacuum apertures;
activating a laser system having a diode coupled to a port through the internal shell of the helmet and configured to shine laser light around the interior of the helmet and on the scalp, the port being separate from the one or more vacuum apertures used in combination with the vacuum system; and
administering a laser therapy to the scalp simultaneously with the alternating of pressures on the scalp, the laser therapy configured to stimulate hair growth;
wherein promoting blood flow while performing laser therapy increases hair growth rates.

10. The method of claim 9, wherein promoting blood flow is achieved through the vacuum system that creates negative pressure against the scalp.

11. The method of claim 9, further comprising:
regulating operation of the vacuum system.

12. The method of claim 9, further comprising:
regulating operation of the laser system.

13. A system for hair treatment, comprising:
a vacuum system configured to apply a negative pressure to a scalp of a user;
a laser system operably associated with the vacuum system and configured to emit a controlled light to the scalp of the user; and
a helmet configured to surround and contact a portion of the scalp, the vacuum system and the laser system being integrally coupled to a portion of the helmet, the helmet having a void space between an internal shell and an external shell;
wherein the internal shell is configured to be adjacent to the scalp, the internal shell having one or more vacuum apertures;
wherein selective operation of the vacuum system and laser system to the scalp is configured to promote the health and growth of hair.

14. The system of claim 13, wherein the vacuum system induces the negative pressure within the void space; and
wherein the negative pressure engages the scalp through one or more of the vacuum apertures.

15. The system of claim 13, wherein the helmet includes a skirting coupled around an external edge of the internal shell, the skirting is configured to form a seal as the vacuum system induces the negative pressure.

16. The system of claim 13, wherein the negative pressure is applied equally across the scalp.

17. The system of claim 13, wherein the laser system emits light within the interior of the internal shell towards the scalp, which in turn promotes hair growth.

18. The system of claim 13, further comprising:
a laser power switch configured to permit a user to select a desired laser power level best suited for the user.

19. The system of claim 13, further comprising:
a vacuum knob configured to permit a user to select the vacuum pressure best suited for the user.

\* \* \* \* \*